United States Patent
Tomita et al.

(10) Patent No.: US 6,514,913 B1
(45) Date of Patent: Feb. 4, 2003

(54) WEED GROWTH INHIBITORY COMPOSITIONS

(75) Inventors: Makoto Tomita, Tokyo (JP); Hirotoshi Tanaka, Tokyo (JP)

(73) Assignee: Marubeni Agrotec Corporation, Tokyo (JP)

( * ) Notice: Subject to any disclaimer, the term of this patent is extended or adjusted under 35 U.S.C. 154(b) by 0 days.

(21) Appl. No.: 09/830,880

(22) PCT Filed: Nov. 1, 1999

(86) PCT No.: PCT/JP99/06077

§ 371 (c)(1), (2), (4) Date: Nov. 2, 2001

(87) PCT Pub. No.: WO00/25585

PCT Pub. Date: May 11, 2000

(30) Foreign Application Priority Data

Nov. 2, 1998 (JP) ............................................ 10-311995

(51) Int. Cl.⁷ ................................................ A01N 47/28

(52) U.S. Cl. ........................................................ 504/332
(58) Field of Search ........................................... 504/332

(56) References Cited

U.S. PATENT DOCUMENTS 4,465,509 A 8/1984 Takematsu et al.
4,579,969 A 4/1986 Takematsu et al.

FOREIGN PATENT DOCUMENTS

JP 61-1415105 7/1986

*Primary Examiner*—S. Mark Clardy
(74) *Attorney, Agent, or Firm*—Browdy and Neimark, P.L.L.C.

(57) ABSTRACT

This invention provides a weed growth inhibitor composition for a lawn grass or an upland farm, comprising an effective amount of 1-(2-chlorobenzyl)-3-(1-methyl-1-phenylethyl)urea (cumyluron) along with a carrier, and a method for inhibiting the growth of weeds, comprising application of the weed growth inhibitor composition to an upland farm or turf.

9 Claims, No Drawings

WEED GROWTH INHIBITORY COMPOSITIONS

REFERENCE TO RELATED APPLICATIONS

The present application is the national stage under 35 U.S.C. §371 of international application PCT/JP99/06077, filed Nov. 1, 1999 which designated the United States, and which application was not published in the English language.

TECHNICAL FIELD

The present invention relates to a novel weed growth inhibitor composition for a lawn grass and an upland farm, and a method for cultivation and management of a lawn grass.

BACKGROUND ART

In golf courses and so on, various lawn grasses, such as Japanese lawn grasses and American or European lawn grasses, are cultivated and managed, and their varieties are numerous. These lawn grasses have varying degrees of resistance to herbicides. Thus, if it is attempted to obtain a sufficient herbicidal effect simultaneously on different varieties of lawn grasses with the use of a single herbicide, phytotoxicity occurs to those varieties of lawn grasses which are poorly resistant. Hence, many types of herbicides are marketed and used according to the varieties of lawn grasses. In upland farms where crops, such as wheat, barley, rye and oats (hereinafter referred to as "wheat and the like") and vegetables, are cultivated, annual weeds mainly occur repeatedly, so that many herbicides for their control are known.

In sowing seeds of a lawn grass to breed turf, early-stage weed control is important. This is because many of weeds developing on the turf occur throughout the year; thus, as the lawn grass grows, the growth of the weeds proceeds, and the effect of a herbicide tends to decline from the viewpoint of weed control. However, application of a herbicide before or after sowing of lawn grass seeds is apt to cause phytotoxicity. Currently, therefore, there is no choice but to apply a herbicide after lawn grass breeding.

Accordingly, a desire has been expressed for a herbicide which, used alone, can produce a sufficient herbicidal effect on many varieties of lawn grasses and crops, and which is safe for lawn grasses and crops such as vegetables without causing phytotoxicity even when applied before or after sowing of lawn grass seeds.

DISCLOSURE OF THE INVENTION

It is an object of the present invention to provide a herbicide composition which can achieve a sufficient herbicidal effect simultaneously on many varieties of lawn grasses and crops alone, and which is safe for lawn grasses without causing phytotoxicity even when applied before or after sowing of lawn grass seeds. It is also another object of the present invention to provide a method for sowing lawn grass seeds and breeding turf with the use of such a herbicide composition.

The inventors of the present invention have conducted extensive studies in an attempt to solve the above-described problems, and found that 1-(2-chlorobenzyl)-3-(1-methyl-1-phenylethyl)urea (hereinafter sometimes referred to as "cumyluron") is highly safe, particularly, for lawn grasses, and shows an unsurpassed effect against annual bluegrass (*Poa annua L.*), flat-sedge (*Cyperus microiria*), etc., which are main turf weeds. They have also found that no phytotoxicity occurs even when cumyluron is applied before or after, or simultaneously with, sowing seeds of a lawn grass, such as ryegrasses (*Lolium SPP.*), to be seeded in breeding turf, and that no phytotoxicity occurs even when the above chemical is applied before or after, or simultaneously with, overseeding seeds of a lawn grass, such as ryegrass, onto an already bred turf.

In regard to weeds occurring in upland farms for cultivation of crops such as vegetables, cumyluron has also been found to exhibit a marked growth inhibiting effect on main weeds, including annual gramineous weeds such as annual bluegrass and foxtail, annual sedge weeds such as flat-sedge (*Cyperus microiria*), and perennial sedge weeds such as purple nutsedge (*Cyperus rotundus*) and *Cyperus brevifolius,* without causing phytotoxicity to wheat, etc. and vegetables.

Therefore, the present invention is a weed growth inhibitor composition for a lawn grass or an upland farm, which comprises cumyluron as an active ingredient.

The present invention is also a weed growth inhibitor composition for a lawn grass or an upland farm, which comprises an effective amount of cumyluron along with a carrier.

Moreover, the present invention is a method for inhibiting the growth of weeds, comprising application of a composition, which comprises an effective amount of cumyluron, to turf or an upland farm.

Furthermore, the present invention is a method for cultivation and management of a lawn grass, comprising application of a composition, which comprises an effective amount of cumyluron, before or after, or simultaneously with, overseeding lawn grass seeds to turf.

PREFERRED EMBODIMENTS FOR CARRYING OUT THE INVENTION

Cumyluron is a known compound disclosed in JP 60-72910 A/1985, JP 5-155710 A/1993, JP 5-155720 A/1993, JP 5-155721 A/1993, JP 5-255018 A/1993, JP 5-255022 A/1993, JP 5-294807 A/1993, JP 5-320011 A/1993, and JP 7-2602 A/1995. In these publications, cumyluron is disclosed only as an active ingredient of a herbicide composition for a paddy field, and its effectiveness as a weed growth inhibitor composition for a lawn grass and an upland farm, especially for a lawn grass, is neither suggested nor disclosed. Hence, a weed growth inhibitor composition for a lawn grass and an upland farm, containing cumyluron as an active ingredient, according to the present invention is novel.

In the present invention, the terms "weed growth inhibitor composition" are interchangeable with the term "herbicide".

The composition of the present invention contains a solid carrier and/or a liquid carrier, and can be present in various forms, such as granules, fine granules, wettable powder, water dispersible granules, emulsifiable concentrate, flowable (suspension concentrate), and dust, which are ordinary forms of agricultural chemicals when in use. For a lawn grass, the composition is often diluted about 1:100 to 1:1000 with water, and applied. Thus, a wettable powder, water dispersible granules, and a flowable are preferred.

The amount of cumyluron which is the active ingredient of the composition of the present invention is generally 0.5 to 95% by weight, preferably 1 to 70% by weight, more preferably 3 to 50% by weight, and most preferably 5 to 50% by weight based on the total weight of the composition, when in the form of granules or fine granules. For a wettable powder or water dispersible granules, the amount of cumyluron is generally 10 to 95% by weight, preferably 20 to 90% by weight, more preferably 30 to 85% by weight, and most preferably 50 to 80% by weight. For a flowable, the amount of cumyluron is generally 1 to 70% by weight, preferably 5 to 65% by weight, more preferably 20 to 60% by weight, and most preferably 30 to 55% by weight.

Examples of the solid carrier include mineral powders such as calcium carbonate, apatite, gypsum, silica gel, vermiculite, mica, diatomaceous earth, talc, pyrophyllite, acid clay, kaolin clay, silica clay, kaolinite, montmorillonite, bentonite, white carbon and pumice powder, plant powders such as microcrystalline cellulose and starch, and polymeric compounds such as polyvinyl chloride, xanthan gum and petroleum resin.

Examples of the liquid carrier include alcohols such as methanol, ethanol, cyclohexanol, amyl alcohol and ethylene glycol, aromatic hydrocarbons such as xylene and methyl naphthalene, halogenated hydrocarbons such as chlorobenzene and trichloroethylene, ethers such as ethyl cellosolve, butyl cellosolve and dioxane, esters such as isopropyl acetate and benzyl acetate, polar solvents such as dimethyl sulfoxide, kerosine, mineral oil, and water.

If necessary, stabilizers or adjuvants in customary use for agricultural chemicals, such as surface active agents, spreaders, and binders, may be formulated, whereby the reliability of the weed growth inhibiting effect can be enhanced.

The weed growth inhibitor composition of the present invention may, if desired, contain an insecticide, a fungicide, a plant growth regulator, a fertilizer, or other herbicide, or can be used in combination with these agents.

The weed growth inhibitor composition of the present invention can be made into a desired form by mixing cumyluron and the above-described carrier and/or the adjuvant or stabilizer, followed by dispersion, suspension, emulsion, granulation, grinding or the like in the customary manner.

The present invention also relates to a method for inhibiting the growth of weeds, comprising application of a composition, which comprises an effective amount of cumyluron, to turf or an upland farm.

The weed growth inhibitor composition of the present invention can be used, as such or diluted, when applied. The amount of application varies according to the scene of application, the time of application, the method of application, the weed targeted, etc. However, the amount of cumyluron applied is generally 50 to 3000 g, preferably 100 to 2000 g, more preferably 200 to 1500 g, most preferably 300 to 1000 g, for 1,000 $m^2$.

For application, the granules, fine granules, or dust can be applied manually as such, or applied by a broadcaster, a power sprayer/spreader or the like. The wettable powder, water dispersible granules, emulsifiable concentrate, or flowable can be diluted with water, and applied by a sprayer, a watering pot or the like.

The application of the weed growth inhibitor composition of the present invention to an upland farm may be performed onto the soil surface after or before sowing seeds or transplanting tubers, seedlings or the like of a crop. Alternatively, the weed growth inhibitor composition can be applied to the surface of the soil, and incorporated into the soil by a tractor, a tiller, a hand spade or the like, before sowing or transplanting.

The composition of the present invention shows an unsurpassed effect against annual gramineous weeds such as annual bluegrass, and annual sedge weeds such as flat-sedge when it is applied from before germination of the weeds until the initial stage of the germination, and potently suppresses the growth of perennial sedge weeds such as purple nutsedge and *Cyperus brevifolius*. The composition of the present invention also has a long-term residual effect.

The "upland farm" in the present invention refers to upland farming agricultural lands and arable lands for cultivating wheat and the like, peas, Chinese cabbage of Shantung type, tomatoes, lettuce, spinach, carrots, Japanese radish, onions, welsh onion, potatoes, corn, etc., and excludes paddy fields. The weed growth inhibitor composition of the present invention has very high safety, particularly, for wheat, peas, Chinese cabbage of Shantung type, tomatoes, lettuce, spinach, carrots, Japanese radish, and onions.

The "lawn grass" herein refers to both of Japanese type lawn grasses and American or European lawn grasses. Examples of the Japanese type lawn grasses include South Japanese lawngrass (*Zoysia matrella*) and Japanese lawngrass (*Zoysia japonica*). Examples of the American or European lawn grasses include ryegrasses, Kentucky bluegrass (*Poa pratensis*), bentgrasses (*Agrostis L.*), and tall fescue (*Festuca arundinacea*). The weed growth inhibitor composition of the present invention is highly safe for lawn grasses, and causes minimal phytotoxicity to both the Japanese type lawn grasses and the American or European lawn grasses. In a golf course, this composition can be used safely in turf including the putting green.

The present invention also relates to a method for cultivation and management of a lawn grass, comprising application of the composition of the present invention before or after, or simultaneously with, overseeding lawn grass seeds to turf.

Techniques for breeding a new lawn grass by overseeding of a reared turf have already been established. For example, South Japanese lawngrass, a Japanese type lawn grass, stops growing in the autumn, and has leaves in the aerial part withered. Thus, seeding with an American or European lawn grass in the autumn to maintain green turf even after autumn is a technique used in many golf courses. Moreover, overseeding with a new variety of lawn grass seeds or the same variety of lawn grass seeds for lawn renewal is used as an ordinary way of turf management.

Under these circumstances, the weed growth inhibitor composition of the present invention can be applied before or after sowing of lawn grass seeds (from before germination until the initial stage of germination), or simultaneously with their sowing, and causes no phytotoxicity to an already bred turf or to a newly seeded turf. That is, it is a weed growth inhibitor composition which can control weeds noxious to a lawn and breed and manage turf, and which is suitable, particularly, for turf.

The following Preparation Examples and Test Examples are provided in order to further illustrate the present invention but should not be construed as limiting the scope thereof. In the Examples, "parts" mean parts by weight.

EXAMPLES

Preparation Example 1: Wettable Powder

50 Parts of cumyluron, 45 parts of kaolin clay, and 5 parts of α-olefin sulfonate were mixed, and the mixture was ground to obtain a wettable powder.

Preparation Example 2: Granules

5 Parts of cumyluron, 60 parts of talc, 32 parts of bentonite, and 3 parts of lignin sulfonic acid were thoroughly ground and mixed, and then 5 parts of water were added. The mixture was fully kneaded, then granulated by an extrusion granulator, and dried to obtain granules.

Preparation Example 3: Flowable

40 Parts of cumyluron, 4 parts of ethylene glycol, 0.1 part of xanthan gum, 5 parts of Solpol 3940 (trade name: commercially available from TOHO CHEMICAL INDUSTRY CO.,LTD.), 1 part of Lunox 1000C (trade name: commercially available from TOHO CHEMICAL INDUSTRY CO.,LTD.), and 53.9 parts of water were thoroughly mixed. The mixture was wet ground to a particle size of 5 microns or less to obtain a flowable.

Next, the excellent inhibitory effect of the weed growth inhibitor composition of the present invention will be demonstrated by the Test Examples.

Test Example 1: Pot Test in Greenhouse

Plastic pots having a size of 100 m²/3000 were filled with soil of an upland farm, and the surface of the soil was flattened. Then, the soil surfaces were sowed with weed seeds of annual bluegrass, foxtail, and flat-sedge. After sowing, the seeds were covered with soil to a height of about 5 mm. Also, the rhizomes of *Cyperus brevifolius* were buried to a depth of about 1 cm. One day after sowing, a predetermined amount of the flowable prepared by the method described in the Preparation Example 3 was applied to the soil surface in an amount of 250 ml/m² of dilution with water. Then, the pots were allowed to stand in the greenhouse, and sprinkled with water at the appropriate times. Thirty days after treatment with the composition, its growth inhibition effect was observed. The results are shown in Table 1. The growth inhibition effect in the table was evaluated according to the following criteria:

Evaluation Criteria for Weed Growth Inhibition Effect:

10:100% inhibition
9:90% inhibition
8:80% inhibition
7:70% inhibition
6:60% inhibition
5:50% inhibition
4:40% inhibition
3:30% inhibition
2:20% inhibition
1:10% inhibition 0: 0% inhibition

TABLE 1

| Amount 0f active ingredient applied (g/1000 m²) | Inhibitory effect | | | |
| --- | --- | --- | --- | --- |
| | annual bluegrass | foxtail | flat-sedge | *Cyperus brevifolius* |
| 0 | 0 | 0 | 0 | 0 |
| 50 | 9 | 9 | 10 | 1 |
| 100 | 10 | 10 | 10 | 5 |
| 250 | 10 | 10 | 10 | 9 |
| 500 | 10 | 10 | 10 | 10 |
| 750 | 10 | 10 | 10 | 10 |
| 1000 | 10 | 10 | 10 | 10 |

Test Example 2: Pot Test in Greenhouse

Plastic pots having a size of 100 m²/5000 were filled with soil of an upland farm, and planted with a lawn sod withdrawn by a hole cutter from various bred turfs. The planted pots were bred and managed in a greenhouse for about 1 month, and then the lawn grasses were cut to the same height to use the pots as sample pots. On the day of the cutting, a predetermined amount of the flowable prepared by the method described in the Preparation Example 3 applied to the sample pots in an amount of 250 ml/m² of dilution with water. Then, the pots were allowed to stand in the greenhouse, and sprinkled with water at the appropriate times. Thirty days after treatment with the composition, its phytotoxicity to the lawn grasses was observed. The results are shown in Table 2. Evaluations of the phytotoxicity to the lawn grasses in the table were made according to the following criteria:

Evaluation Criteria for Phytotoxicity:

−:None
±:Very slight
+:Slight
2+:Moderate
3+:Heavy
×:Dead

TABLE 2

| Amount of active ingredient applied (g/1000 m²) | Lawn phytotoxicity | | | | | | |
| --- | --- | --- | --- | --- | --- | --- | --- |
| | South Japanese lawngrass | Japanese lawngrass | Bent-grass | Kentucky bluegrass | Bermuda-grass | Perennial ryegrass | Tall fescue |
| 0 | − | − | − | − | − | − | − |
| 100 | − | − | − | − | − | − | − |
| 250 | − | − | − | − | − | − | − |
| 500 | − | − | − | − | − | − | − |
| 750 | − | − | − | − | − | − | − |
| 1000 | − | − | − | − | − | − | − |
| 2000 | − | − | − | − | − | − | − |

Test Example 3: Field Test

A land of breeding of bentgrass was divided into plots of 1 m² (1×1 m), and a predetermined amount of the flowable prepared by the method described in the Preparation Example 3 was applied in an amount of 250 ml/m² of dilution with water. Thirty and sixty days after treatment with the composition, its phytotoxicity to the lawn was observed. To manage the heights of the lawn grasses, lawn mowing was carried out at the appropriate times. The results are shown in Table 3. Evaluations of the phytotoxicity to the lawn in the table were made according to the aforementioned criteria.

TABLE 3

| Amount of ingredient applied (g/1000 m²) | Lawn phytotoxicity (bentgrass) | |
| --- | --- | --- |
| | 30 days after treatment | 60 days after treatment |
| 0 | — | — |
| 300 | — | — |
| 600 | — | — |
| 1200 | — | — |
| 2400 | — | — |

Test Example 4: Field Test: Lawn Grass Seed Overseeding Test

A land of breeding of South Japanese lawngrass was divided into plots of 1 m² (1×1 m), and seeds of perennial ryegrass or tall fescue, and seeds of annual bluegrass as a weed were sowed on the entire surface of each plot. On the day of sowing, a predetermined amount of the flowable prepared by the method described in the Preparation Example 3 was applied in an amount of 250 ml/m² of dilution with water. Thirty days after treatment with the composition, its weed growth inhibition effect and lawn phytotoxicity were observed. The results are shown in Table 4. Evaluations of the weed growth inhibition effect and lawn phytotoxicity in the table were made according to mentioned criteria.

TABLE 4

| Amount of active ingredient applied (g/1000 m$^2$) | Lawn phytotoxicity | | | Inhibitory effect |
|---|---|---|---|---|
| | Overseeded lawn grass | | Bred lawn grass | |
| | Perennial ryegrass | Tall fescue | South Japanese lawngrass | annual bluegrass |
| 0 | — | — | — | 0 |
| 100 | — | — | — | 10 |
| 250 | — | — | — | 10 |
| 500 | — | — | — | 10 |
| 750 | — | — | — | 10 |
| 1000 | — | — | — | 10 |

Test Example 5: Test for Phytotoxicity to Crops

Plastic pots having a size of 954 cm$^2$ were filled with soil of an upland farm, and the surface of the soil was flattened. Then, seeds of wheat, pea, Chinese cabbage of Shantung type, tomato, lettuce, spinach, carrot, Japanese radish, and onion were sowed onto the pots. Then, the sowed seeds were covered with soil until the seeds were hidden and water was sprinkled to start the test. Three days after sowing, a predetermined amount of the wettable powder prepared by the method described in the Preparation Example 1 was uniformly applied to the sample pots in an aomount of 30 ml /pot of dilution with water. The test was conductedd in a greenhouse, and water was sprinkled as desired. Twenty-nine days after treatment with the composition, its phytotoxicity to the crops was observed. The results are shown in Table 5. Evaluations of the crop phytotoxicity in the table were made according to the aforementioned criteria.

TABLE 5

| Crop name | Amount of active ingredient (g/1000 m$^2$) | Crop phytotoxicity |
|---|---|---|
| Wheat | 0 | — |
| | 75 | — |
| | 150 | — |
| | 240 | — |
| | 480 | — |
| | 960 | — |
| Peas | 0 | — |
| | 75 | — |
| | 150 | — |
| | 240 | — |
| | 480 | — |
| | 960 | — |
| Chinese cabbage 0f Shantung type | 0 | — |
| | 75 | — |
| | 150 | — |
| | 240 | — |
| | 480 | — |
| | 960 | — |
| Tomatoes | 0 | — |
| | 75 | — |
| | 150 | — |
| | 240 | — |
| | 480 | — |
| | 960 | — |
| Lettuce | 0 | — |
| | 75 | — |
| | 150 | — |
| | 240 | — |
| | 480 | — |
| | 960 | — |
| Spinach | 0 | — |

TABLE 5-continued

| Crop name | Amount of active ingredient (g/1000 m$^2$) | Crop phytotoxicity |
|---|---|---|
| | 75 | — |
| | 150 | — |
| | 240 | — |
| | 480 | — |
| | 960 | — |
| Cucumber | 0 | — |
| | 75 | — |
| | 150 | — |
| | 240 | — |
| | 480 | — |
| | 960 | — |
| Carrots | 0 | — |
| | 75 | — |
| | 150 | — |
| | 240 | — |
| | 480 | — |
| | 960 | — |
| Japanese radish | 0 | — |
| | 75 | — |
| | 150 | — |
| | 240 | — |
| | 480 | — |
| | 960 | — |
| Onions | 0 | — |
| | 75 | — |
| | 150 | — |
| | 240 | — |
| | 480 | — |
| | 960 | — |

INDUSTRIAL APPLICABILITY

The weed growth inhibitor composition of the present invention shows an unsurpassed effect against low spear grass, etc., which are main weeds against lawn, is highly safe for lawn, and can be used assuredly for wide varieties of lawn grasses. Moreover, the use of the weed growth inhibitor composition of the present invention makes it easy and convenient to cultivate and manage lawn grasses. Particularly for turf to be overseeded, the weed growth inhibitor composition contributes greatly to a saving in labor concerned with weed control. The weed growth inhibitor composition of the present invention also has high safety for various upland crops, and facilitates weed control.

What is claimed is:

1. A method for inhibiting growth of annual gramineous weeds, comprising applying a composition comprising an effective amount of 1-(2-chlorobenzyl)-3-(1-methyl-1-phenylethyl)urea to turf or an upland farm.

2. The method of claim 1, comprising:
applying the composition to said annual gramineous weeds in turf.

3. A method for cultivation and management of annual gramineous weeds in lawn grass, comprising applying a composition containing an effective amount of 1-(2-chlorobenzyl)-3-(1-methyl-1-phenylethyl)urea to annual gramineous weeds in turf.

4. A method for inhibiting growth of annual gramineous weeds in turf grass or an upland farm crop, comprising applying to said annual gramineous weeds in said turf grass or upland farm crop an amount sufficient for said inhibiting said growth of a compound of 1-(2-chlorobenzyl)-3-(1-methyl-1-phenylethyl)urea at an application rate applied to said turf or said upland farm of an amount of said compound of 50 to 3,000 g/1000 m$^2$.

5. The method of claim 4 wherein said application rate is 100 to 2,000 g/1000m$^2$.

6. The method of claim 4 wherein said application rate is 200 to 15,000 g/1000m$^2$.

7. The method of claim 4 wherein said application rate is 300 to 1,000 g/1000 m$^2$.

8. The method of claim 4 wherein said crop is selected from the group consisting of wheat, peas, Chinese cabbage, tomatoes, lettuce, spinach, carrots, radish and onions.

9. The method of claim 4 wherein said turf grass is selected from the group consisting of ryegrass, Kentucky bluegrass, bentgrass and tall fescue.

* * * * *